(12) United States Patent
Holmberg et al.

(10) Patent No.: US 6,203,522 B1
(45) Date of Patent: *Mar. 20, 2001

(54) METHOD AND CONNECTION UNIT FOR STERILE TRANSFER OF SOLUTION VIA A CONNECTOR

(75) Inventors: Bengt Holmberg, Bjarred; Sven Jonsson, Staffanstorp, both of (SE)

(73) Assignee: Gambro AB (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/259,960

(22) Filed: Mar. 1, 1999

Related U.S. Application Data

(63) Continuation of application No. 08/793,349, filed as application No. PCT/SE95/00795 on Jun. 28, 1995, now Pat. No. 5,879,328.

(30) Foreign Application Priority Data

Aug. 23, 1994 (SE) .................................................. 9402805

(51) Int. Cl.$^7$ .................................................. A61M 37/00
(52) U.S. Cl. .............................................. 604/82; 604/85
(58) Field of Search .............................. 604/4–6, 82, 283, 604/905, 85, 28, 29, 537, 533; 285/3, 21, 425, DIG. 16, DIG. 2; 83/171; 422/25, 28, 905

(56) References Cited

U.S. PATENT DOCUMENTS

| 4,022,205 | 5/1977 | Tenczar . |
| 4,030,494 | 6/1977 | Tenczar . |
| 4,673,400 | 6/1987 | Martin . |
| 5,879,328 | * 3/1999 | Holmberg et al. ..................... 604/82 |

FOREIGN PATENT DOCUMENTS

| 0 116 986 | 8/1984 | (EP) . |
| 0 230 864 | 8/1987 | (EP) . |
| 428009 | * 5/1991 | (EP) . |
| 0 428 009 | 5/1991 | (EP) . |
| 0 588 375 | 3/1994 | (EP) . |

* cited by examiner

Primary Examiner—Sharon Kennedy
(74) Attorney, Agent, or Firm—Lerner, David, Littenberg, Krumholz & Mentlik, LLP

(57) ABSTRACT

Methods for the sterile transfer of a solution are disclosed, including sterilizing the inlet to a connector by flowing a sterilizing fluid around the connector inlet, sterilizing a penetrating element for the connector by flowing a sterilizing solution around the penetrating element, and penetrating the sterilized inlet by the sterilized penetrating element in order to transfer the solution through the penetrating element on the connector. Apparatus for such sterile transfer of a solution is also provided.

8 Claims, 5 Drawing Sheets

METHOD AND CONNECTION UNIT FOR STERILE TRANSFER OF SOLUTION VIA A CONNECTOR

This application is a continuation of U.S. application Ser. No. 08/793,349 filed Feb. 20, 1997, which is a 371 of PCT/SE95/00795 filed Jun. 28, 1995.

FIELD OF THE INVENTION

The present invention relates to a method and a connection unit for the sterile transfer of solution through a connector.

BACKGROUND OF THE INVENTION

The present invention is intended to be used in conjunction with an on-line sterilizing arrangement, such as described European Application No. 428,009. This application describes a continuous heat sterilizing arrangement in which a solution is heated during transport in a conduit to a high temperature, for example about 130° C., and is maintained at this temperature for a predetermined period in order to effect sterilization. Thereafter, the solution is cooled to the temperature at which it is to be used. The sterilization step takes place at a high pressure, which is achieved with a pump and throttle arrangement.

A heat exchanger is generally used in this system to provide the heat energy. The sterilization arrangement is used for sterilizing infusion solutions such as Ringer's solution, other medical solutions such as dialysis solutions, purified water to obtain sterilized water, or other such solutions.

The sterilizing arrangement according to European Application No. 428,009 is provided with a shunt conduit which in principle connects the inlet to the outlet so that the solution which is in the system can be circulated in a closed circuit. In this manner, the temperature of the circulating solution can be raised to, for example, 120° C. in order to sterilize the device itself.

The solution which has been sterilized with the above-described sterilizing arrangement can be used directly, for example in dialysis or infusion. In certain circumstances it is also desirable to transfer the sterilized solution to storage bags for later use, or for delivery to other departments within the hospital. For this purpose, disposable sets of tubes are available which terminate with a bag.

Normally, such bags are filled with a medical solution, whereafter the set of tubes is sealed and the disposable article is then sterilized in its entirety, i.e. with the medical solution within the bag. Such sterilizing can be effected with gamma-sterilization or by means of autoclaving.

Alternatively, the set of tubes can be provided with a medical solution after the set of tubes has been sterilized. In such cases, a sterile connector is normally used which comprises a membrane which is broken when used. Those parts which are connected together are sterile. With such a sterile connector, there is always the risk that bacteria which may reside on the outer side of the membrane are introduced with the connector device and contaminate the interior of the connector.

European Application No. 230,864 describes a sterile connection of two containers in which the connection takes place in a sterilized chamber which is maintained under aseptic conditions by means of a chemical disinfectant. Chemical disinfection, however, does not guarantee sterility, and at the same time the risk for bacteria contamination is still present.

SUMMARY OF THE INVENTION

In accordance with the present invention, these and other objects have now been realized by the invention of a method for the sterile transfer of a solution from a first location associated with a penetrating element to a second location through a connector having an inlet, the method comprising sterilizing the inlet of the connector by flowing a sterilizing solution around the inlet of the connector, sterilizing the penetrating element by flowing a sterilizing solution around the penetrating element, and penetrating the sterilized inlet by the sterilized penetrating element so as to transfer the solution from the first location to the second location through a connector.

In accordance with one embodiment of the method of the present invention, the sterilizing of the inlet of the connector and the sterilizing of the penetrating element both comprise heat sterilizing. Preferably, the heat sterilizing is carried out at a temperature of greater than about 120° C. Most preferably, the heat sterilizing is also carried out at a pressure of greater than about 2 atmospheres (absolute pressure).

In accordance with another embodiment of the method of the present invention, the sterilizing of the inlet of the connector and the sterilizing of the penetrating element are carried out simultaneously by use of the same sterilizing solution. In a preferred embodiment, the method includes maintaining the penetrating element and the inlet of the connector within a common bore, and circulating the sterilizing solution in a closed circuit including a heater for the sterilized solution. Most preferably, the method includes sterilizing the common bore and sealing at least a portion of the sterilized common bore with the inlet of the connector during the penetrating step.

In accordance with the apparatus of the present invention, apparatus is provided for the sterile transfer of a solution from a first location associated with an inlet to the apparatus to a second location through a connector having an inlet, the apparatus comprising a housing defining a bore in fluid communication with the inlet, the connector being insertable into the bore, a penetrating element disposed within the bore, recirculation means for recirculating a sterilizing solution around the penetrating element and the inlet of the connector located within the bore, and activation means for causing the penetrating element to penetrate the inlet of the connector within the bore whereby the solution can be transferred from the first location to the second location.

In accordance with one embodiment of the apparatus of the present invention, the apparatus includes sealing means for sealing a portion of the penetrating element and the inlet of the connector sterilized by the sterilizing solution. In a preferred embodiment, the sealing means also acts to seal the recirculation means when the activation means causes the penetrating element to penetrate the inlet of the connector, thereby creating a closed sterilized region.

In accordance with another embodiment of the apparatus of the present invention, the apparatus includes heating means for heating the sterilizing solution to a temperature of greater than about 120° C. In a preferred embodiment, the apparatus also includes pressure means for increasing the pressure of the sterilizing solution to a pressure of greater than about 2 atmospheres (absolute pressure).

In accordance with another embodiment of the apparatus of the present invention, the sealing means comprises a cover over the inlet of the connector, whereby the penetrating element penetrates the cover when the activation means causes the penetrating element to penetrate the inlet of the connector.

The object of the present invention is to provide both a method and a connection unit which permit sterile connection for transfer of a sterilized solution to a previously sterilized disposable set of tubes in a manner such that bacterial contamination is completely eliminated. The set of tubes can end with a connection bag, or may lead to an infusion device or a dialysis machine or other medical equipment.

BRIEF DESCRIPTION OF THE DRAWINGS

The present invention is described in greater detail in the following detailed description, which includes reference to the embodiments of the invention shown in the drawings, in which.

DETAILED DESCRIPTION

Figure 1:
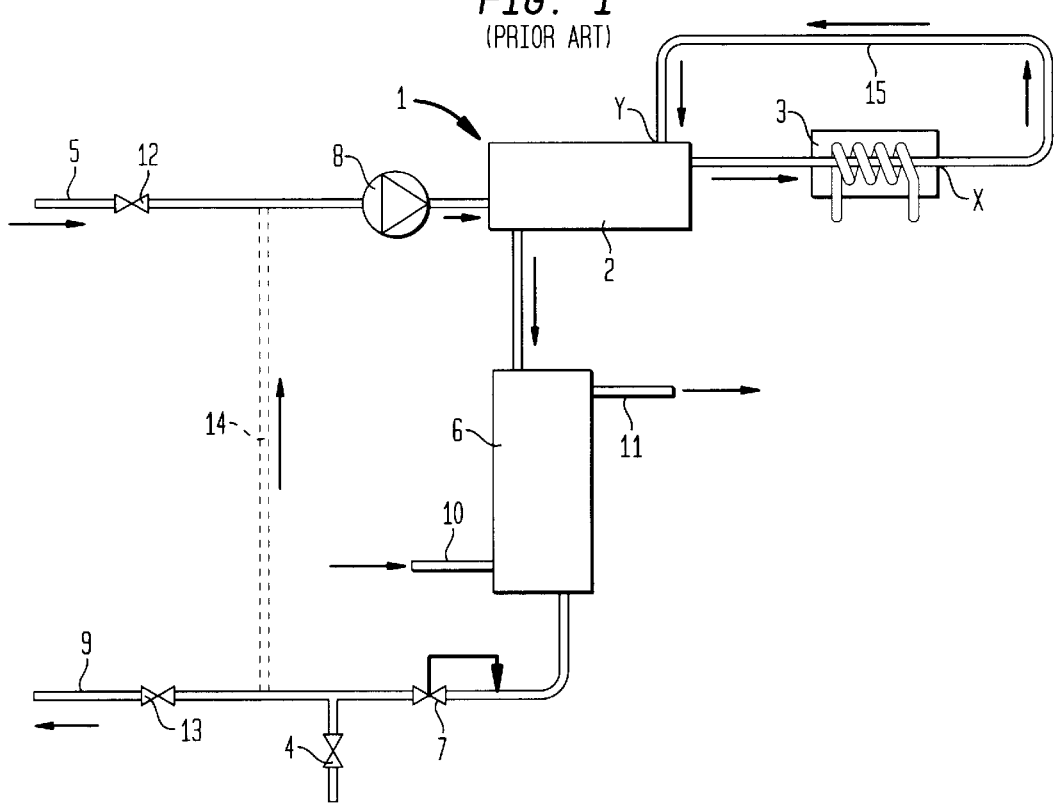
FIG. 1 is a schematic representation of the sterilizing arrangement according to European Application No. 428,009.

A sterilizing arrangement according to European Application No. 428,009 is shown in FIG. 1. A solution which is to be sterilized is introduced through inlet 5 and flows through a valve 12 to a pump 8. The pump 8 increases the pressure of the solution and pumps the solution to a first heat exchanger 2.

The solution passes across the primary side of the heat exchanger 2 and is fed to a heating arrangement 3. The solution is transported from the heating arrangement 3 in a delay conduit 15 of a length such that the residence time permits sterilizing of the solution which has been heated by the heating arrangement 3.

The solution is then fed from the conduit 15 to the heat exchanger 2 where the solution passes across the secondary side of the heat exchanger and heats the incoming solution on the primary side.

The solution is transported from the heat exchanger 2 to a second heat exchanger 6, and passes across its primary side. A heating medium is provided on the secondary side of the heat exchanger 6, which heating medium can be cold water if further cooling is required, and which flows from an inlet 10 to an outlet 11. The solution flows from the heat exchanger 6 by means of a throttle arrangement 7 and a valve 13 to an outlet 9.

A shunt conduit 14 is connected between the inlet 5 downstream of the valve 12 and the outlet 9 upstream of the valve 13. The function of the shunt conduit 14 is to allow recirculation of the solution in the system without any new solution being introduced through the inlet 5 or removed by the outlet 9. By shutting off the cooling means supply to the second heat exchanger 6, the solution in the closed circulating system can be heated to a high temperature, for example 120° C., for sterilizing the system.

In addition, a bleed valve 4 is arranged downstream of the throttle valve 7 and upstream of the outlet valve 13.

Figure 2:
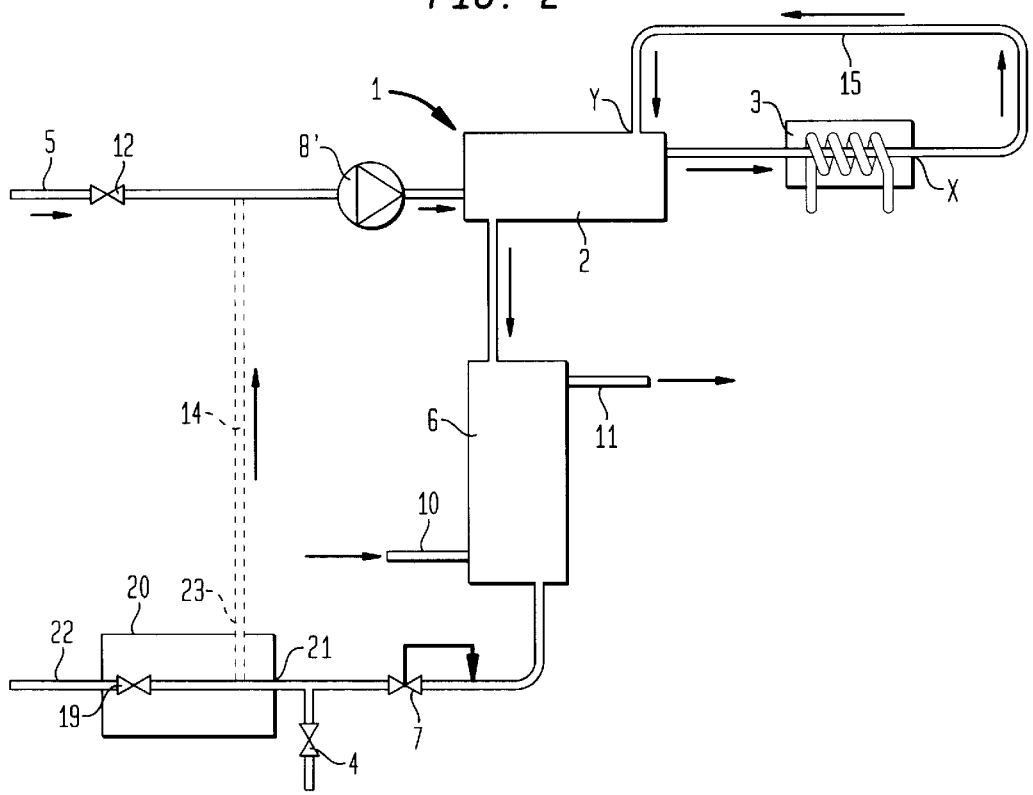
FIG. 2 is a representation similar to that of FIG. 1, showing, however, the connection of a connecting unit according to the present invention therein.

The connection unit 20 according to the present invention is arranged in cooperation with the shunt conduit 14 and shown in FIG. 2. The connection unit has an inlet 21 for incoming solution from the throttle valve 7, an outlet 23 for solution which is to be recirculated in the shunt conduit 14 and an outlet 22 for exiting sterile solution.

Figure 3:
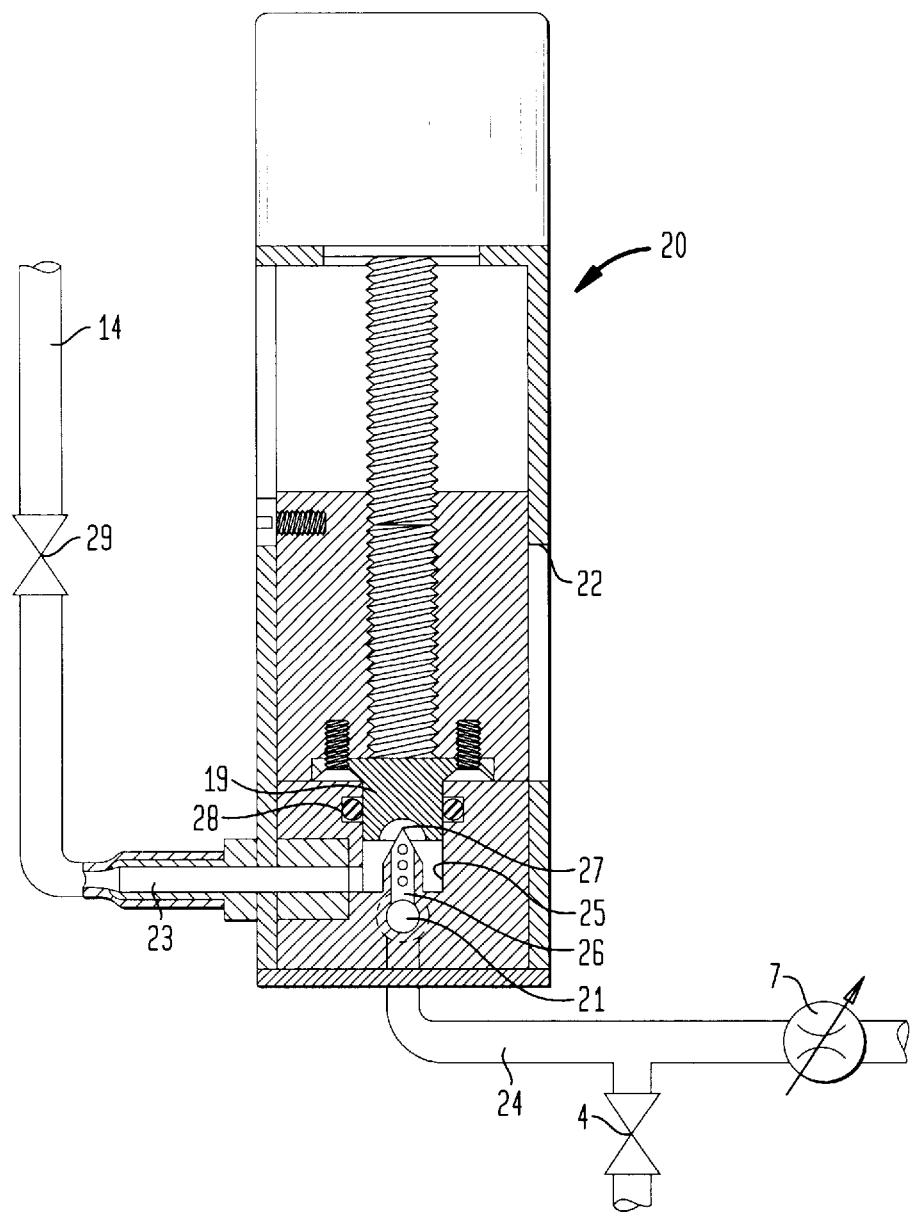
FIG. 3 is a side, elevational, cross-sectional view of the connection unit of the present invention, in a stand-by position.

In FIG. 3, the connection unit 20 according to the present invention is shown in a stand-by position. The connections of the various conduits according to FIG. 2 are shown in FIG. 3. Accordingly, there is an inlet 21 (positioned behind the unit 20 in FIG. 3) which is connected to the throttle valve 7 and the bleed valve 4. In addition, there is an outlet 23 to the shunt conduit 14. A piston 19 is shown in a closed position and closes the opening 22 which will be explained in greater detail below.

The inlet 21 opens into a cylindrical bore 25 through a tube 26 which is concentric with the bore 25 and which terminates with a penetration element in the form of a point 27. Solution from the throttle valve 7 can thus be fed through the inlet conduit 24 to the inlet 21 and subsequently to the tube 26 and, through the point 27, into the bore 25 and further through the outlet 23 to the shunt conduit 14.

In FIG. 3, the bore 25 is sealed at its upper end by the piston 19 which cooperates with an O-ring seal 28 arranged in the side of the bore.

The operation in the stand-by position as shown in FIG. 3 thus permits the sterilizing arrangement according to European Application No. 428,009 to be used with recirculation according to the present invention.

Figure 4:
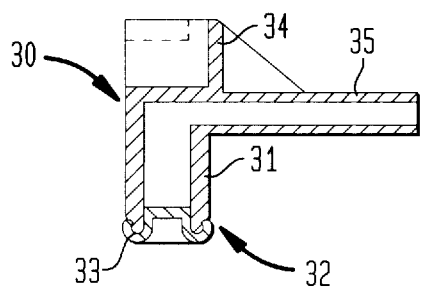
FIG. 4 is a side, elevational, cross-sectional view of a connector intended to be used in accordance with the present invention.
Figure 5:
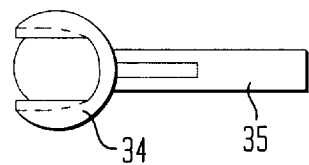
FIG. 5 is a top, plan view of the connector according to FIG. 4.

When the connection unit 20 is to be used for filling of a disposable set of tubes, a connector 30 as shown in FIGS. 4 and 5 is used. FIG. 4 is a cross-sectional view taken through the connector. The connector consists of a cylinder 31 of a diameter such that it fits in the bore 25 and seals against the O-ring 28. At the lower region of the cylinder 31 there is a reduced portion 32 on which a cover 33 is arranged. The cover 33 can be of rubber. In addition, the connector 30 has a semi-cylindrical-shaped engagement portion 34 of such dimension that the piston 19 fits therein. Finally, a connection portion 35 is provided to which a tube is connected. The tube leads to a container which is to be filled or some other suitable device, such as a dialysis machine. In FIG. 5, the connector 30 is seen from above.

Figure 6:
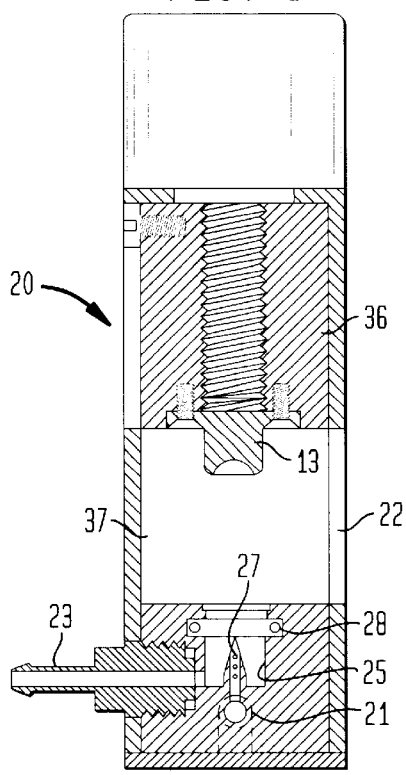
FIG. 6 is a side, elevational view similar to that of FIG. 3, showing the connection unit of the present invention in an open position for introduction of the connector according to FIG. 4 therein.

The connection unit according to the present invention can be used to fill a container connected to the connector 30. This takes place in the following manner (see FIGS. 6–8). Firstly, it is assured that the connecting unit is depressurized by means of opening the bleed valve 4. Thereafter, the piston 19 is displaced by means of an activating device 36, to the position shown in FIG. 6. By means of this displacement of the activating device 36, an opening 22 is revealed in the side of the connection unit which leads to a cavity 27. The bore 35 opens into this cavity. Accordingly, the opening to the bore 25 is exposed.

The connector 30 is introduced through the opening 22 so that the lower region 32 is located immediately above the bore 25 and can be downwardly displaced into the bore 25 so that the cylinder 31 cooperates with the O-ring 28. This position is shown in FIG. 7.

The correct introduction of the connector into the bore 25 is facilitated by means of the engagement portion 34 cooperating with the piston 19 and snap fastening therewith during the insertion of the connector 30 through the opening 22. Thereafter, the activating device is displaced downwardly to the position shown in FIG. 7.

Figure 7:
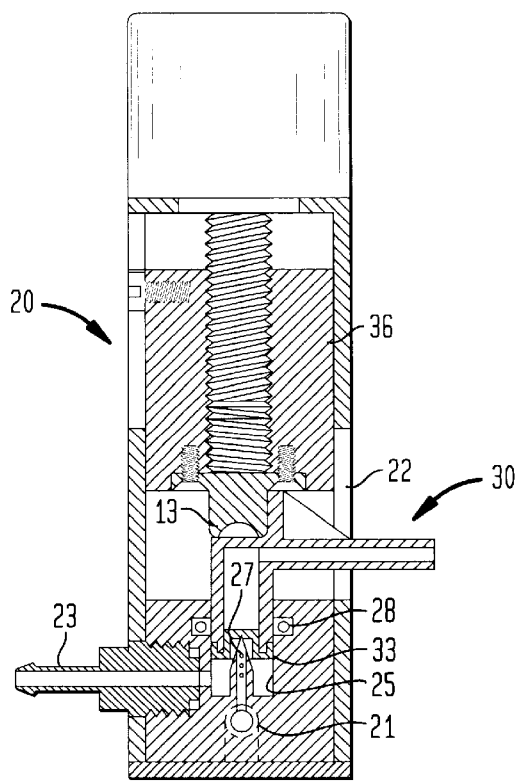
FIG. 7 is a side, elevational view similar to that of FIG. 6, showing the connection unit of the present invention with in situ connector in a sterilizing position.

As is evident from FIG. 7, the connector 30 is only partially introduced into the bore 25. The connector 30 is introduced into the bore 25 by a distance such that the O-ring 28 cooperates with the cylindrical surface of the connector 30 so that sealing of the bore 25 is achieved. At the same time, the connector 30 is so high up that the point 27 does not reach the cover 33 on the connector 30.

The sterilizing arrangement according to FIG. 2 has a particular sterilizing position in which the solution is heated to a high temperature, for example 120° C. This is achieved by means of cold water no longer being supplied to the secondary side of the second heat exchanger 6, and the heating arrangement 3 being operated so that the temperature in the recirculating system increases to 120° C. In this manner, the pressure in the entire circulation conduit rises to a pressure of about 2 atmospheres (absolute pressure, i.e. an overpressure of one atmosphere). This pressure arises automatically, since the valves 12 and 13 are closed.

In the position shown in FIG. 7, the sterilizing arrangement is activated so that a solution with a temperature of about 120° C. circulates through the conduit 24, inlet 21, tube 26 and point 27 to the bore 25, and may flow around the cover 33 of the connector 30, and further through the outlet 23 to the shunt conduit 14 as described above. This position is maintained for as long as it requires for the bore 25 and the lower portion of the connector 30 to become sterilized.

When a sufficiently long period of time has elapsed for the sterilization to have been achieved, the drainage valve 4 is activated and the sterilizing arrangement is adjusted so that solution which is to be sterilized is introduced through the inlet 5, and is allowed to flow through the system. For this to occur, the shunt conduit 14 is closed by means of the valve 29 (see FIG. 3). The bleed valve 4 is open until normal operation is attained in the system.

Figure 8:
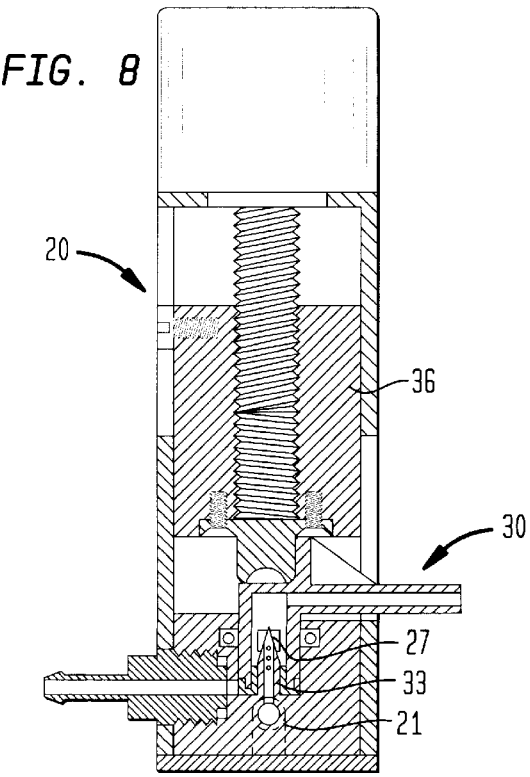
FIG. 8 is a side, elevational view, similar to that of FIG. 6, showing the connection unit of the present invention in a filling position.

When normal operation is attained, the activating device 36 is activated to press the connector 30 downwardly to its lower position as shown in FIG. 8 at the same time that the valve 4 is closed. In this position, the point 27 penetrates the cover 33 so that access is gained to the interior of the connector. At the same time, the outer peripheral portions of the cover 30 seal against the base of the bore so that the outlet 23 is closed off. In this manner, all solution which enters through the inlet 21 has to flow into the connector 30 and to a connected storage bag or dialysis machine or other medical equipment.

By means of this embodiment of the connecting unit hereof, the outer portion of the connector 25 and the point 27 are sterilized before these two parts cooperate with each other. In this manner, the risk of bacteria entering the connector 30 when the cover or membrane 33 is penetrated is totally eliminated.

When filling of a storage bag is completed, the bag is sealed in a suitable manner, for example by means of heat welding in a known manner.

It is also possible to make the cover 33 of a rubber material provided with slots which seal in a sterile manner after removal of the point 27. Such a connector is previously known from European Application No. 116,986.

As has been previously mentioned, the sterilizing solution is heated to a high temperature, for example about 121° C. The pressure in the bore 25 thus becomes about 2 atmospheres. In order to assure sterility, it is necessary that circulation continues for about 20 minutes.

It may be desirable to reduce this time, and this can be achieved by increasing the temperature to, for example, 130° C. and a pressure of 2.7 atmospheres. In this manner, the time can be reduced to about two minutes. It must be ensured, however, that the hot sterilizing solution reaches all the regions which are to be sterilized.

As is apparent from FIG. 3, the cover 33 is provided with a depression in which the point 27 is positioned during the sterilizing cycle. The region which must be sterilized is this depression as well as the region of the cover which forms the seal against the base of the bore 25. In addition, the actual penetrating part 27 must be sterilized. An effective sterilizing at high temperature can be attained if the point 27 is shaped as a cone provided with a plurality of small holes. The sterilizing solution will thus spray the inside of the depression of the cover 33 which will thereby be intensely treated with sterilizing solution.

It is preferred that the cover 33 be made from a material which tolerates high temperatures up to at least about 150° C. The remaining part of the connector 33 can be more or less effectively insulated from the warm sterilizing solution, for example by means of the cover 33, which extends a certain amount upwardly along the cylindrical outer surface of the connector.

Figure 9:
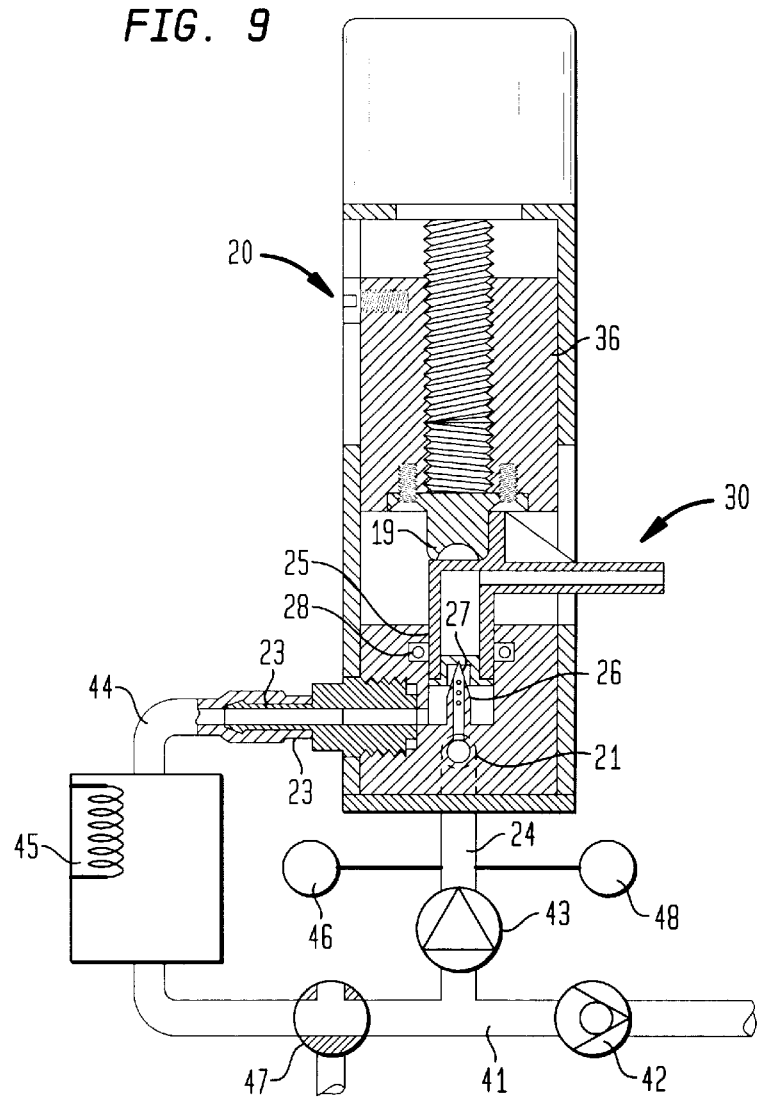
FIG. 9 is a side, elevational, cross-sectional view similar to that of FIG. 3, showing the connection unit of the present invention in another adaptation.

The connection unit according to the present invention can of course be used independently of the sterilizing arrangement, as is apparent from European Application No. 428,009. Thus, an arrangement can be used as shown in FIG. 9. The sterile solution which is to be transferred to a container through the connector 30 is fed through a conduit 41 and a non-return valve 42. A pump 43 feeds the sterile solution in the conduit 41 to the inlet 21. When the connection unit is in the sterilizing position shown in FIG. 9, the solution which is introduced through the conduit 21 has to flow out through the outlet 23 to the shunt conduit 44. The shunt conduit 44 extends through a heating arrangement 45 back to the inlet of the pump 43.

When the pump 43 is actuated, the solution circulates in a closed circuit through the inlet 21 and the bore 25 to the outlet 23 by means of the shunt conduit 44 and the heating arrangement 45 back to the pump 43. No further solution can be introduced through the inlet 41.

When the cover 33 of the connector 30 and the bore 25, as well as the penetrating element 27, are to be sterilized, the heating arrangement 45 is activated and heats the solution which circulates in the circuit to a temperature of about 120° C. The pressure in the circulating solution rises but because of the non-return valve 42 the solution does not boil. When the solution has circulated at 120° C. for a sufficiently long time, for example about 20 minutes, the heating arrangement 45 is disconnected and the still circulating solution is allowed to cool. When a sufficiently low temperature has been attained, which is measured by a temperature sensor 46, the activating device 36 is activated to press the connector 30 to the position shown in FIG. 8. The temperature at which this activation occurs is dependent on the material of the connector 30. If PVC-material is used, it is preferred that the temperature has decreased to at least about 80° C. Measurements can alternatively be carried out using a pressure sensor 48, possibly in combination with the temperature sensor 46.

When the connector 30 is pushed down to its bottom position, the cover 33 seals the outlet 23 so that the circulation in the conduit 44 ceases. The pump 43 continues to operate and thereby draws solution from the conduit 41 through the non-return valve 42 and feeds the solution through the inlet 21 and the connector 30 to a storage bag or the like connected to the connector 30.

The sterilizing of the penetrating member 27 and the connector 30 can take place using the sterile solution which is introduced through the conduit 41, and which is heated with the heating arrangement 45.

Alternatively, pure water can be circulated in the circulation circuit 44. When the sterilizing is completed, a valve 47 is adjusted which is shown with dashed lines in FIG. 9 and the contents of the pump 43, the inlet 21, the bore 25 and the outlet 23 can pass to an outlet at the same time as the sterile solution which is to be fed in passes through the conduit 41, the pump 43, the inlet 21 and to the bore 25 and further through the outlet 23. At the same time, the pressure drops to about atmospheric pressure. When a sufficiently long time has expired for all the water to have been replaced, the activating device 36 is activated so that filling is initiated.

Figure 10:
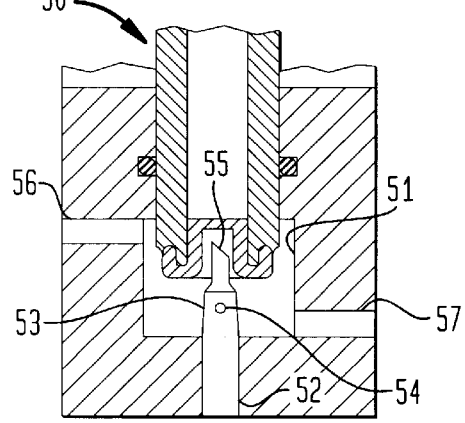
FIG. 10 is an enlarged, partial, side, cross-sectional view of a portion of the connection unit of the present invention according to an alternative embodiment threof.

An alternative embodiment of the bore 25 is shown in FIG. 10. Thus, the bore is provided with a lower expansion 51. In this manner, the sterilizing solution will circulate around the entire lower portion of the connector 30 so that it becomes sterilized. This embodiment is suitable if the connector 30 is made from a material which tolerates temperatures in the order of about 120° C. without deformation, such as polycarbonate.

Furthermore, the penetrating element 52 is provided with a conical region 53 which, when activation of the activating device and downward displacement of the connector 30 take place, cooperates with the cover or seal 33 of the connector at the same time that cooperation occurs with the base of the bore. In this manner, the region which must be sterile to allow sterile transfer to be able to take place is further restricted.

In order to facilitate the recirculation, the conical region 52 is provided with a plurality of holes 54 so that the sterilizing solution can flow through the tip 55 of the penetrating element as well as through the opening 54. In this manner, a larger circulation flow is maintained during the sterilizing phase.

Two outlets 56 and 57 corresponding to the outlet 23 are shown in FIG. 10. These outlets can be tangentially arranged to ensure the best flow properties in the bore 25. It is also possible to use the conduit 56 as an inlet as well as the inlet 52 in order to further increase the flow. Further variations will be apparent to a skilled person. A further variant of the present invention is shown in FIG. 11, which can be used to connect a bag containing sterile solution to a machine in which the sterile solution is to be used, for example a dialysis machine or an infusion tube.

Figure 11:
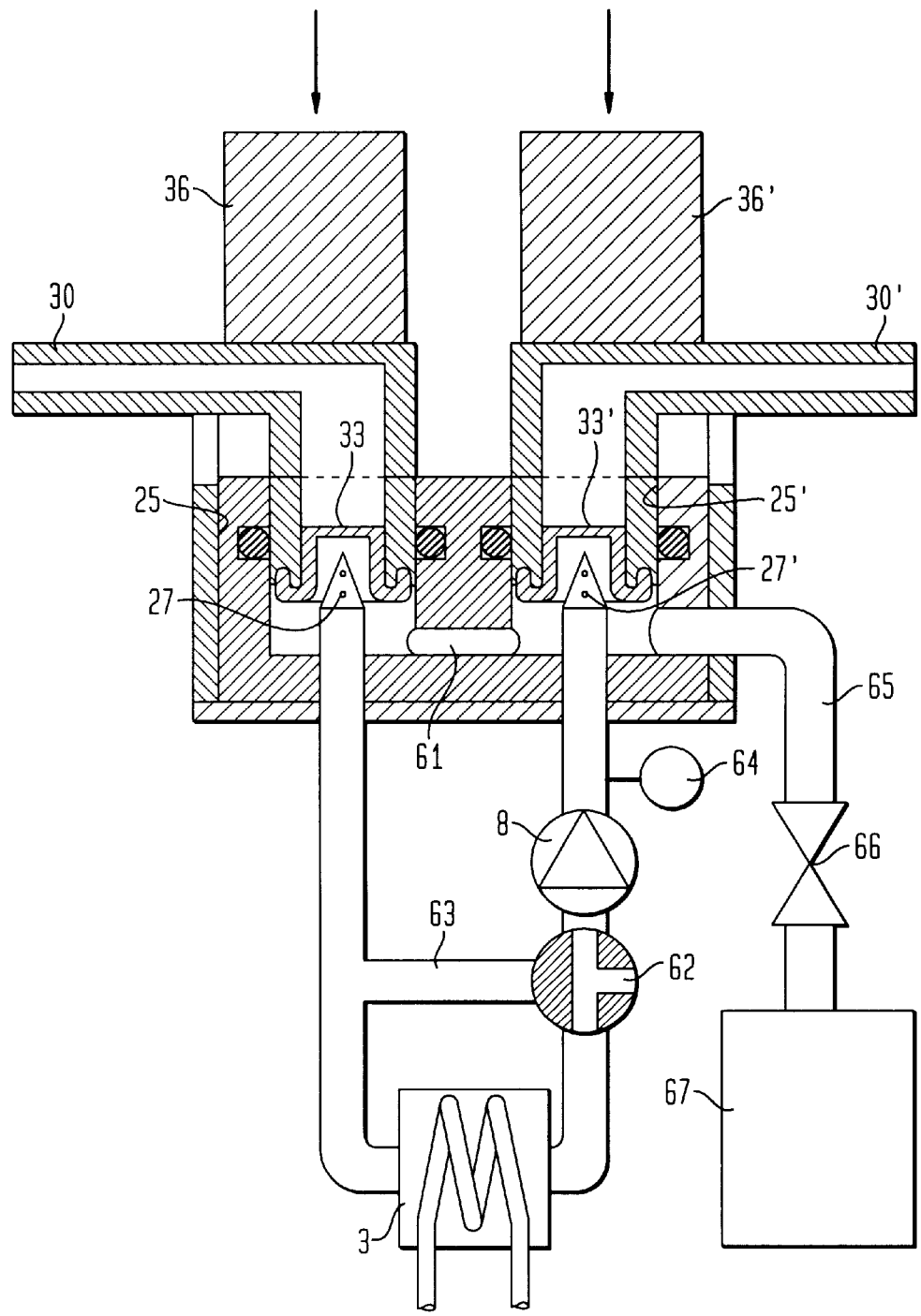
FIG. 11 is a side, elevational, partially cross-sectional view, similar to that of FIG. 3, showing a further adaptation of the connection unit of the present invention.

The sterile solution is in a storage bag or a device which is connected by means of a connector 30 shown on the left in FIG. 11. The connector 30 is connected to a connector 35 of a user who is to use the sterile solution. The two connectors 30 and 30' are each inserted in respective bores 25 and 25' with respective points 27 and 27'. The bores 25 and 25' are connected to each other by means of a communication passage 61. During the sterilizing phase, a solution, which can be water, is circulated by the pump 8 to the tip 27', around the cover 33', into the bore 25' and through the communication passage 61 to the other bore 25, further around the cover 33, to the point 27 and by means of the heating arrangement 3 back to the pump 8. By activating the heating arrangement 3, the circulating solution is heated to about 121° C. In this manner, an inner pressure of about 2 atmospheres is reached. When the thus initiated sterilizing has gone on for about 20 minutes, a valve 62 is switched before the pump 8 to its second position so that the heating arrangement 3 is by-passed by the conduit 63. The circulation continues until the temperature which is sensed by a temperature sensor 64 has fallen to a safe temperature, for example about 60° C.

The second bore 25' is connected to a valve 66 and a flexible storage bag 67 through a conduit 65.

When the temperature has dropped to a suitable level, the activating device 36 is activated on the left-side connector 30 and presses the connector 30 down to its lower position. This causes the point 27 to penetrate the cover 33 and the cover 33 seals the passage 61 and the bore 25. A sterile connection between the connector 30 with the point 27 has thus been attained.

The sterile solution which is supplied by the connector 30 flows through the point 27, the conduit 63, the valve 62 and the pump 8 to the point 27'. The solution flows from the point 27' further to the bore 25'. Since the conduit 61 is closed at its left end by means of the cover 33, the solution cannot pass through the conduit 61. Instead, the solution flows through the conduit 65 through the now open valve 66 to the storage bag 67.

When a sufficient quantity of sterile solution has flowed along this path and has displaced all solution which has been used for sterilizing, which occurs after approximately one minute, the activating device 36' is activated and connects the connector 30' with the point 27' which penetrates the cover 33' which simultaneously seals against the base of the bore 25'. In this manner, the conduit 25 is sealed off whereby the valve 66 can be closed. A sterile connection between the connector 30 and the connector 30' has now been attained.

In the embodiment of the connection unit which is shown in FIGS. 3–9, the bore 25 is preferably arranged in a heat-insulating material such as polycarbonate. In this manner, the regions of the connector 30 above the cover 33 are prevented from being heated to a great degree during the sterilizing phase. This makes it possible for cheap material for the connector 30, such as PVC, to be used without the risk of deformation during the sterilizing phase.

The sterile solution can be infusion solutions, dialysis solutions or other medical solutions such as physiological sodium chloride solution, and the like.

The sterile solution can also be water, which is filled in bags through the connector. The bags contain a salt in powder form and are sterilized by suitable means so that the interior of the connector, the bags and their contents are sterile. When the bags are to be used, they are connected to the sterilizing arrangement 1 according to FIG. 2 and water is added to the bags. In this manner, the salt is dissolved and a medical solution is provided ready for use. The salt can contain several substances, such as a concentrate which is used in hemodialysis. The salt can also contain further substances, such as medically active substances in connection with infusion.

Suitably, the sterile solution itself is also used for the sterilizing phase. That portion of the sterile solution which has been used for sterilizing can be disposed of and new sterile solution used for filling the connector.

As has been mentioned above, a particular solution such as physiological sodium chloride solution or water can be used for the heat-sterilizing phase of the connector's outer portion, whereafter the solution is disposed of and replaced by the sterile solution which is to be added to the connector, such as dialysis solution, peritoneal dialysis solution (containing i.e. glucose) infusion solution, and the like.

The invention is not restricted to the above-described embodiment but can be modified within the scope of the invention in a manner obvious for the skilled person. The various described components can be combined in other ways than those which have been shown in the drawings.

What is claimed is:

1. Apparatus for the sterile transfer of a solution from a first location to a second location, said apparatus comprising a housing having an inlet in fluid communication with said first location, a sterilizable connector having an inlet for insertion into and removal from said housing, recirculation means for recirculating a sterilizing solution into said housing through said housing inlet for sterilizing said housing inlet of said sterilizable connector inlet when said sterilizable connector is inserted into said housing and in order to supply said solution to said second location through said sterilizable connector, and heating means for heating said sterilizable solution to a temperature of greater than about 120° C.

2. The apparatus of claim 1 wherein said housing includes a bore in fluid communication with said housing inlet, whereby said sterilizable connector can be inserted into said bore and said recirculation means also sterilizes said bore.

3. The apparatus of claim 1 including pressure means for increasing the pressure of said sterilizing solution to a pressure of greater than about 2 atmospheres (absolute pressure).

4. The apparatus of claim 2 wherein said sterilizable connector includes a closed penetrable portion for insertion into said housing, whereby said sterilizable connector is sealed from the atmosphere when inserted into said bore.

5. The apparatus of claim 1 wherein said housing includes a sterile solution outlet for insertion of said sterilizable connector thereinto.

6. The apparatus of claim 4 wherein said bore includes an O-ring, whereby said sterilizable connector seals against said O-ring upon insertion into said bore.

7. The apparatus of claim 1 wherein said housing includes an outlet, and said recirculation means circulates said sterilizable solution through said outlet for return to said inlet.

8. Apparatus for the sterile transfer of a solution comprising a housing having an inlet and containing a penetrating member, a sterilizable connector having an inlet for insertion into said housing to a predetermined position adjacent to said penetrating member and an outlet, said inlet including a penetrable seal for sealing said sterilizable connector from the atmosphere, circulation means for circulating a sterilizing solution into said housing to said predetermined position whereby said sterilizing solution can sterilize said penetrating member and said inlet of said sterilizable connector, and means for causing said penetrating member to penetrate said penetrable seal, whereby said sterilizing solution can flow through said sterilizable connector.

* * * * *

UNITED STATES PATENT AND TRADEMARK OFFICE
CERTIFICATE OF CORRECTION

PATENT NO. : 6,203,522 B1
DATED : March 20, 2001
INVENTOR(S) : Holmberg et al.

It is certified that error appears in the above-identified patent and that said Letters Patent is hereby corrected as shown below:

<u>Title page,</u>
<u>Item [63],</u>
After "08/793,349" insert -- filed February 20, 1997, which is a 371 of --
Delete "filed as application No.".

<u>Column 1,</u>
Delete lines 5 through 7 in their entirety, and insert therefor
-- REFERENCES TO CROSS RELATED APPLICATIONS
The present application is a continuation of prior Application No. 08/793,349, filed on February 20, 1997, now U.S. Patent No. 5,879,328, which is based upon International Application No. PCT/SE95/00795, filed on June 28, 1995, which claims priority from Swedish application No. 9402805-7, filed August 23, 1994. --

Signed and Sealed this

Thirtieth Day of October, 2001

Attest:

NICHOLAS P. GODICI
Attesting Officer
Acting Director of the United States Patent and Trademark Office